United States Patent [19]
Chu

[11] Patent Number: 5,850,832
[45] Date of Patent: Dec. 22, 1998

[54] LARYNGEAL MASK AIRWAY INSERTION GUIDE

[76] Inventor: Kyo Y. Chu, P.O. Box 690099, Stockton, Calif. 95269

[21] Appl. No.: 880,798
[22] Filed: Jun. 23, 1997
[51] Int. Cl.⁶ .................................................. A61M 16/00
[52] U.S. Cl. ............................... 128/200.26; 128/207.14; 128/207.15
[58] Field of Search ......................... 128/200.26, 207.15, 128/207.18, 207.14, 206.29; 604/264

[56] References Cited

U.S. PATENT DOCUMENTS

| | | | |
|---|---|---|---|
| 2,463,149 | 3/1949 | Caine | 128/200.26 |
| 4,589,410 | 5/1986 | Miller . | |
| 4,825,858 | 5/1989 | Frankel . | |
| 5,065,755 | 11/1991 | Klafta . | |
| 5,174,283 | 12/1992 | Paskey | 128/200.26 |
| 5,203,320 | 4/1993 | Augustine | 128/200.26 |
| 5,277,178 | 1/1994 | Dingley | 128/200.26 |
| 5,529,582 | 6/1996 | Fukuhara . | |
| 5,682,880 | 11/1997 | Bogin | 128/200.26 |

FOREIGN PATENT DOCUMENTS 3037708   4/1982   Germany .

Primary Examiner—John G. Weiss
Assistant Examiner—V. Srivastava
Attorney, Agent, or Firm—Richard C. Litman

[57] ABSTRACT

An laryngeal mask airway (LMA) insertion guide comprising a flexible, elongated and curved member having a rounded top end portion that serves as a handle, a bottom end that forms a rounded, flat and curved scoop, a curved fulcrum member that extends from the bottom proximate surface near the scoop, and a curved holder member that extends from the top distal surface. Each component of the insertion guide is fashioned to engage a respective LMA component, and the device curves to facilitate proper insertion and placement of the LMA in the larynx of the patient. In use, an anesthesiologist fits the LMA insertion guide onto the LMA and inserts them together into the larynx of patient, and uses the holder and scoop to bend the LMA while simultaneously using the fulcrum to push the LMA down into the patient's throat. The slender, curvilinear member permits removal of the LMA guide without widening the device or otherwise complicating its backward passage through the throat and mouth of the patient, making it safer for insertion therein, and more efficient for anesthesiologist use.

9 Claims, 3 Drawing Sheets

LARYNGEAL MASK AIRWAY INSERTION GUIDE

BACKGROUND OF THE INVENTION

1. Field of the Invention

The present invention relates to medical devices and, more specifically, to an insertion guide for facilitating the placement of a laryngeal mask airway in a patient's larynx.

2. Description of Related Art

To maintain an oral airway during anesthetic management or the like, conventionally a laryngoscope has been used as a method of endotracheal intubation. Recently, there is also known a method of using a laryngeal mask airway 15 (LMA), as shown in FIG. 3A (PRIOR ART), which can be inserted into the larynx.

The LMA 15 is made up of an oval mask body 11 and a hollow cuff 13 which engages the periphery of the mask body 11. A respiratory tube 17 is connected to a tube connecting portion 17a on the outside surface (i.e., the wrong side as opposed to the right side) of the mask. The respiration is performed through the holes 11a which are formed in the mask body 11. A tube 19 for injecting air into the cuff 13 connects to the cuff. Prior to insertion of the LMA 15, an anesthesiologist or other medical professional deflates the cuff 13 by extracting air therefrom. Once the anesthesiologist inserts the LMA 15 into a patient's larynx, he or she then inflates the cuff 13 by introducing air therein. In this manner, an airway is maintained by covering the larynx with the LMA 15.

During insertion of the LMA 15 into the larynx, it is normal practice to bend the head of the patient backwards, push the LMA along his or her palatine wall to prevent the LMA 15 from twisting, and urge the LMA 15 into position. In order to do so, it is necessary for the anesthesiologist to insert their fingers into the patient's oral cavity, resulting in a fear of infection of the anesthesiologist. Therefore, for the purpose of preventing infection, medical professionals will wear rubber gloves. However, according to the FDA (Food and Drug Administration) of the U.S.A. in July, 1991, the occurrence of allergy through the use of rubber gloves has become a problem, resulting in a dilemma for the health care professional and a felt need for an instrument for inserting an LMA.

U.S. Pat. No. 5,529,582 discloses multiple embodiments of an apparatus for inserting an LMA. In one embodiment, a pair of clamping bars extends from a holder, and have connecting front parts to form an abutment adapted for the front end of an LMA. A band piece extends from the abutment along the clamp bars and towards the holder, with a ring for pulling it towards the holder. Operation of this embodiment of the device of '582 involves pinchingly holding the LMA 15 between the clamping bars at a tube-connecting portion 17a, and inserting the LMA into the larynx. The anesthesiologist then forces the tube-connecting portion 17a out from the space between the clamp bars by releasing the pressure exerted on them and removes the device, leaving the LMA inside the larynx.

The second embodiment of the apparatus of '582 has a forceps-like structure, having a pair of contoured and pivoted clamp bars. An abutment portion on the front ends of the clamp bars abuts the front end of the outside surface of the LMA. In use, an anesthesiologist closes the clamp bars towards each other on opposing sides of the tube-connecting portion 17a of the LMA 15, and pinchingly engages it to insert the LMA into the larynx. The anesthesiologist then forces the tube-connecting portion out from the space between the clamp bars by releasing the pressure exerted on them and removes the device, leaving the LMA inside the larynx.

While both embodiments of the apparatus of '582 provide an anesthesiologist with a way of inserting an LMA without using their fingers, they also possess problematic features that adversely affect LMA insertion. Both embodiments have a pair of clamp bars that closely engage the top and bottom of the LMA respiratory tube, but extend an appreciable distance from opposing sides of the middle of the tube, adding to the overall girth of what the anesthesiologist must insert into a patient's larynx. This widening action by the clamp bars on the LMA tube make insertion more difficult, especially in patients having narrow or deep throats.

Furthermore, the bifurcated clamp design of the devices disclosed in '582 complicates an anesthesiologist's manipulation of these devices during LMA insertion. The bulkiness of the device of '582, with its curvilinear clamp bars, makes proper location of the LMA difficult, especially in deep-throated patients and patients having narrow throats. Also, to disengage the clamp bars from the LMA tube, the anesthesiologist must urge the clamp bars apart, further widening the overall girth of the device while it is still within the patient's larynx. This widening makes the procedure involving the devices of '582 more difficult for the anesthesiologist, and more dangerous for the patient.

Despite their curvilinear shape, the clamp bars of the embodiments of '582 do not sufficiently conform to the curvature of the LMA tube, making manipulation of the tube awkward and imprecise for the anesthesiologist. Furthermore, the inflexibility of the clamp bars adversely affects an anesthesiologist's proper handling and optimum placement of the LMA, with its flexible components.

Other inventions and patents are less related to LMA insertion, but involve endotracheal tube insertion. U.S. Pat. No. 4,589,410, for example, describes an endotracheal tube that includes an insertion cord and ring to control the tube's curl during intubation. The automatic endotracheal intubation device of U.S. Pat. No. 4,825,858 includes a flexible guide that curves and an adapter component. Furthermore, U.S. Pat. No. 5,065,755 discloses a protective sheath for an endotracheal tube, and German Patent 3,037,708 discloses a hooked instrument for endotracheal intubation. However, none of these inventions or patents deal specifically with LMA insertion.

In light of the shortcomings of the above inventions and patents, there is a need for an LMA insertion guide device. There is also a need for an easy-to-use and easily removable insertion guide for anesthesiologists to use in placing an LMA in the larynx of a patient. There is also a need for a device to assist an anesthesiologist in the proper and safe handling and optimum placement of an LMA. There is also a need for a flexible LMA insertion guide that conforms to the curvature of the LMA tube.

None of the above inventions and patents, taken either singly or in combination, is seen to describe the instant invention as claimed.

SUMMARY OF THE INVENTION

An alternative method of maintaining an oral airway during the administration of anesthesia involves using a laryngeal mask airway (LMA), which can be inserted into the larynx. The LMA comprises a mask body having a peripheral cuff and a respiratory tube that connects to a connecting portion on the outside surface of the mask. Prior to insertion of the LMA, an anesthesiologist or other medical professional deflates the cuff and inflates it after insertion to cover the larynx and ultimately maintain an airway. Insertion of the LMA involves the anesthesiologist inserting their fingers into the patient's oral cavity, resulting in a fear of infection.

The device of the present invention operably engages an LMA upon its insertion into the larynx of a patient, serving as a guide for an anesthesiologist in this procedure. The LMA insertion guide comprises a flexible, elongated and curved member having a substantially circular cross section and distal and proximate surfaces respective to an anesthesiologist inserting the LMA. A rounded top end serves as a handle, while a bottom end forms a rounded, flat and curved scoop that fits the distal surface of LMA mask body. A curved fulcrum member extends from the bottom proximate surface near the scoop, and snugly fits over the tube-connecting portion of the LMA. A curved holder member extends from the top distal surface, above the fulcrum, and fits over the portion of the LMA respiratory tube farthest from the LMA mask body. The device curves to define an angle that facilitates proper insertion and placement of the LMA in the larynx of the patient.

In use, an anesthesiologist fits the LMA insertion guide onto the LMA and inserts them together, into the larynx of patient. The curvature of the elongated member emulates that of the LMA, closely conforming to the respiratory tube and LMA mask body, simplifying the simultaneous insertion of the LMA and LMA guide.

In properly placing the LMA in the patient's larynx, the anesthesiologist uses the holder and scoop to bend the LMA and simultaneously uses the fulcrum to push the LMA down into the patient's throat. The angle and shape of the scoop also affords better manipulation of the LMA tip at the larynx for proper positioning thereof.

Removal of the LMA guide from the LMA involves disengaging the holder and fulcrum from their respective points thereon, whereupon the LMA guide can be withdrawn from the patient's throat. The slender, curvilinear member permits removal of the LMA guide without widening the device or otherwise complicating its reverse passage through the throat and mouth of the patient, making it safer for insertion therein, and more efficient for anesthesiologist use.

Accordingly, it is a principal object of the invention to provide an LMA insertion guide device.

It is another object of the invention to simplify the insertion and removal of a guide for anesthesiologists to use in placing an LMA in the larynx of a patient.

It is a further object of the invention to promote an anesthesiologist's proper and safe handling and optimum placement of an LMA.

Still another object of the invention is to provide a flexible LMA insertion guide that conforms to the curvature of the LMA tube.

It is also an object of the invention to provide improved elements and arrangements thereof in an apparatus for the purposes described which is inexpensive, dependable and fully effective in accomplishing its intended purposes.

These and other objects of the present invention will become readily apparent upon further review of the following specification and drawings.

BRIEF DESCRIPTION OF THE DRAWINGS

Similar reference characters denote corresponding features consistently throughout the attached drawings.

DETAILED DESCRIPTION OF THE PREFERRED EMBODIMENT

Figure 1:
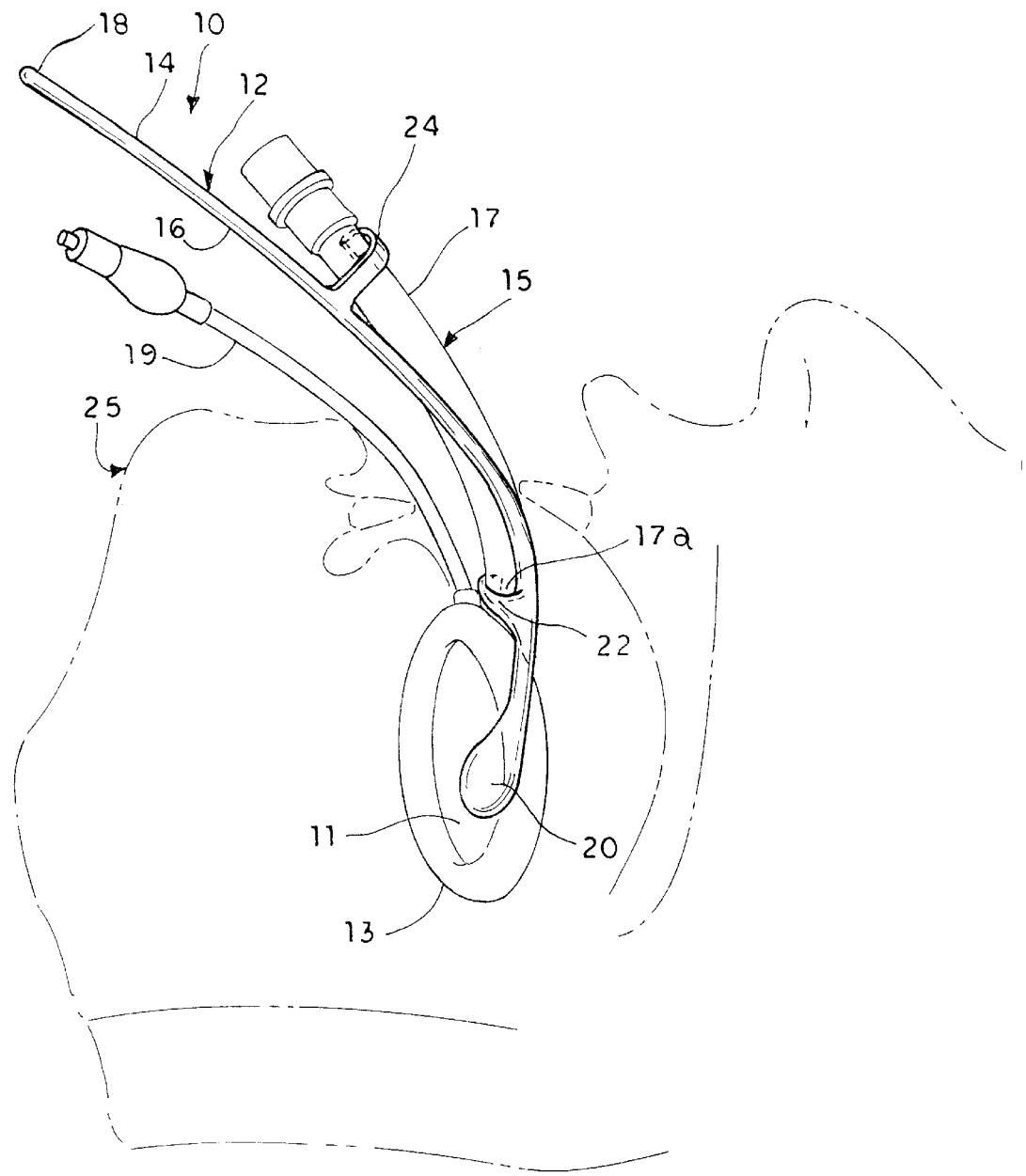
FIG. 1 is a side environmental view of the guide device of the present invention, in use during the insertion of a laryngeal mask airway.
Figure 2:
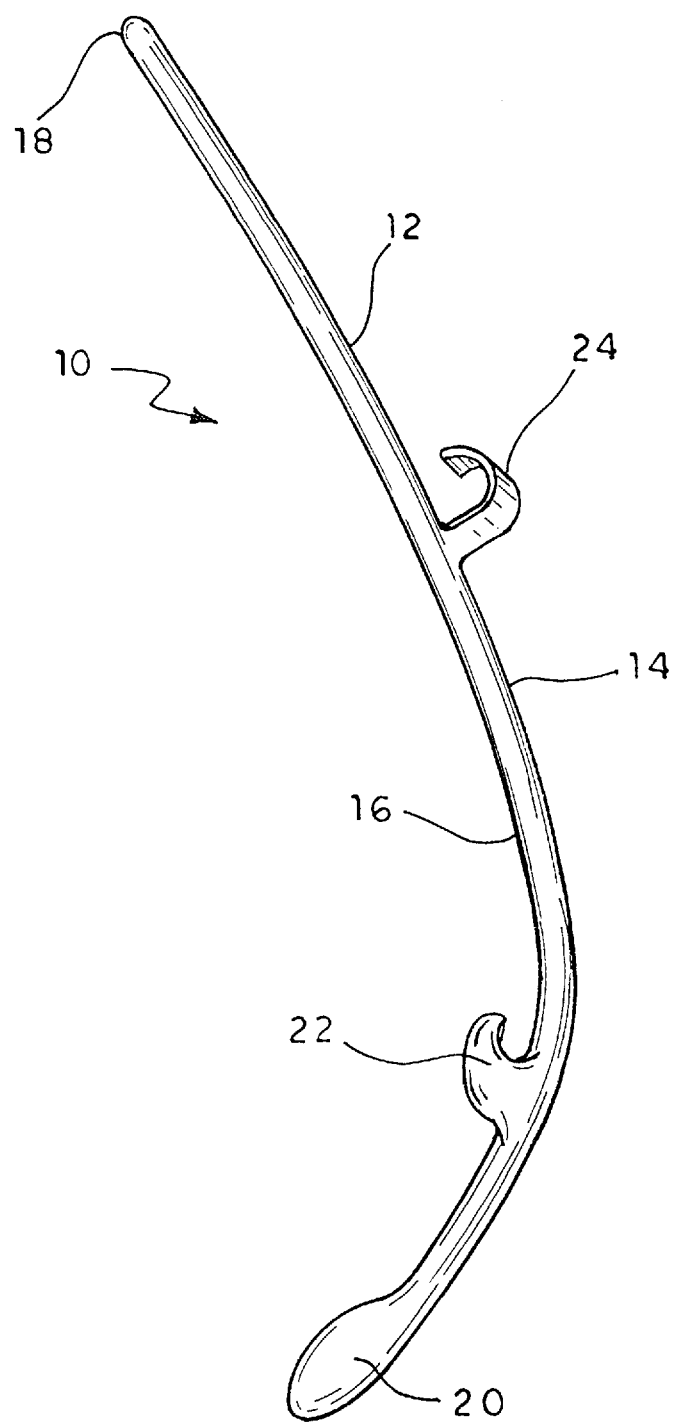
FIG. 2 is a side perspective view of the laryngeal mask airway guide device of the present invention.
Figures 3A, 3B:
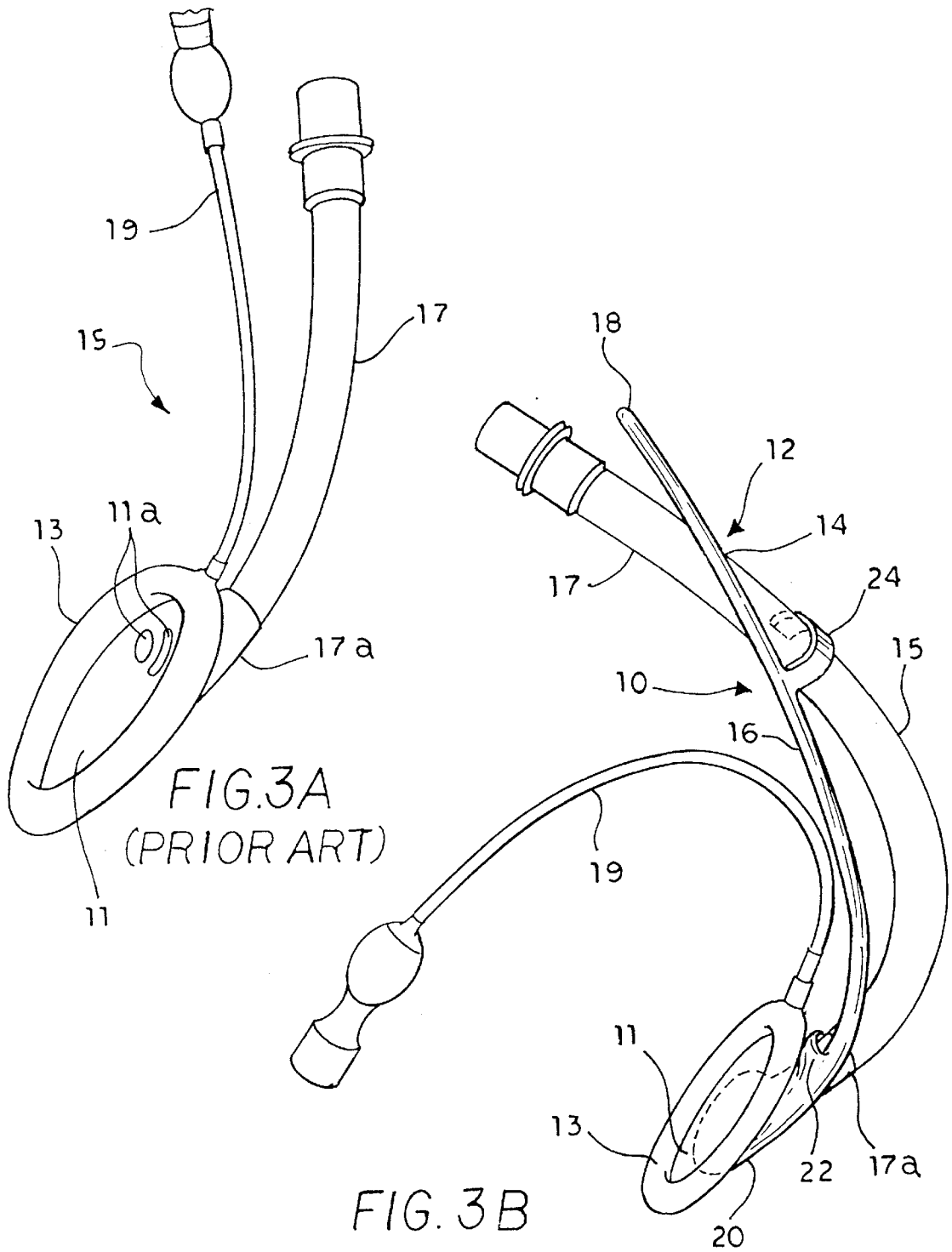
FIG. 3A shows a typical laryngeal mask airway of the prior art.
FIG. 3B is a side view showing the guide device of the present invention in place on a laryngeal mask airway of FIG. 3A.

The present invention, referenced as 10 herein, is shown in FIG. 1 operably engaging an LMA 15 upon its insertion into the larynx of a patient 25. Now referring to FIG. 2, the LMA insertion guide 10 comprises an elongated curved member 12, having a substantially circular cross section. Member 12 is preferably fabricated from a rigid material having flexible qualities, such as a plastic or a composite having shape-memory. Member 12 has opposing distal and proximate surfaces 14,16, the surfaces being defined respective to an anesthesiologist inserting the LMA 15. A rounded top end portion 18 of member 12 serves as a handle for an anesthesiologist to use in manipulating insertion guide 10. A bottom end portion 20 forms a scoop. Scoop 20 is rounded, flat and curved, so as to fit the distal surface of LMA mask body 11, as shown in FIG. 1 and FIG. 3B.

A curved fulcrum member 22 extends from proximate surface 16 of member 12, near scoop 20. Fulcrum 22 is dimensioned to snugly fit over the tube-connecting portion 17a of the LMA 15. Between scoop 20 and fulcrum 22, member 12 curves to conform to the distal portion of the LMA 15, as shown in FIG. 3B. A curved holder member 24 extends from the distal surface 14 of member 12, closer to top end portion 18 than fulcrum 22. Holder 24 is dimensioned to fit over the portion of LMA respiratory tube 17 farthest from LMA mask body 11, also shown in FIG. 3B. Between fulcrum 22 and holder 24, member 12 curves to best facilitate insertion of the LMA 15, and preferably defines an angle of approximately 120° formed by two segments tangential with diverging portions of member 12 between scoop 20 and fulcrum 22. This angulation is most effective for proper insertion and placement of the LMA 15 in the larynx of the patient 25. Furthermore, FIG. 2 shows both fulcrum 22 and holder 24 curving to the anesthesiologist's left side, making it easier for a right-handed person to control and manipulate the device. Alternatively, both fulcrum 22 and holder 24 curve to the anesthesiologist's right side.

In use, an anesthesiologist fits LMA insertion guide 10 onto the LMA 15 by securing fulcrum 22 in place on the tube-connecting portion 17a of the LMA 15 and by simultaneously securing holder 24 in place on the portion of the LMA respiratory tube 17 farthest from LMA mask body 11, so that scoop 20 engages the distal portion of the LMA mask body 11. The anesthesiologist then inserts the LMA 15 with LMA guide 10, into the larynx of the patient 25, using rounded top end portion 18 as a handle, as shown in FIG. 1. The curvature of member 12 emulates that of the LMA 15, closely conforming to the respiratory tube 17 and LMA mask body 11, ultimately making it easier for the anesthesiologist to insert the LMA 15 and LMA guide 10 simultaneously.

Once the LMA 15 has been inserted, the anesthesiologist uses LMA guide 10 to properly place LMA 15, specifically the LMA mask body 11, within the patient's larynx. In doing so, the anesthesiologist uses holder 24 and scoop 20 to bend the LMA 15, shown bent in FIG. 3B, and simultaneously uses fulcrum 22 to push the LMA 15 down into the patient's throat, to insure proper placement therein. The angle and shape of scoop 20 also allows an anesthesiologist to better manipulate the tip of the LMA 15 at the larynx and position it properly there.

After the anesthesiologist positions the LMA 15 so that it covers the larynx of patient 25, he or she can disengage holder 24 and fulcrum 22 from their respective points on the LMA 15 by angularly rotating the device, whereupon he or she can easily remove LMA guide 10 from the throat of the patient 25, leaving the LMA 15 in place. The slender, curvilinear structure of member 12 allows the anesthesiologist to remove LMA guide 10 without widening the device or otherwise complicating its backward passage through the throat and mouth of patient 25, thereby making it safer for insertion therein, and more efficient for anesthesiologist use.

It is to be understood that the present invention is not limited to the sole embodiment described above, but encompasses any and all embodiments within the scope of the following claims.

I claim:

1. An insertion guide device for use in the insertion of a laryngeal mask airway (LMA) into the throat of a patient, wherein a LMA comprises a respiratory tube, a tube-connecting portion and a mask body, said insertion guide comprising:
    a unitary, elongated member, having a distal surface and a proximate surface defining a top end portion, a bottom end portion, and a curved portion, whereby said insertion guide conforms to the length and the contour of the respiratory tube, the tube-connecting portion and the mask body in order to removably engage the LMA upon its insertion into a patient's throat, wherein said elongated member includes
        first member means for removably engaging the tube-connecting portion, said first means extending from said proximate surface;
        second means for removably engaging the respiratory tube, said second means extending from said distal surface; and,
        third means for removably engaging the mask body integrally extending from said bottom end portion.

2. The insertion guide device according to claim 1, wherein elongated member is constructed of a flexible material having a shape-retaining memory.

3. The insertion guide device according to claim 1, wherein said third means comprises a scoop member having rounded, curved and flat surfaces for engaging a distal surface of the mask body.

4. The insertion guide of device according to claim 1, wherein said first means comprises a fulcrum member extending from and connecting to said proximate surface, including a curved surface for fitting the tube-connecting portion of the LMA, and projecting laterally from said elongated member.

5. The insertion guide device according to claim 4, wherein said second means comprises a holder member extending from and connecting to said distal surface of said elongated member at a point above said fulcrum member, having a curved surface for fitting the respiratory tube and said holder member projecting laterally in the same direction as said fulcrum member.

6. The insertion guide device according to claim 1, wherein said top end portion is a rod having a rounded end.

7. An insertion guide device for use in the insertion of a laryngeal mask airway (LMA) into the throat of a patient, wherein a LMA comprises a respiratory tube, a tube-connecting portion and a mask body, said insertion guide comprising:
    a unitary, elongated member, constructed of a flexible material having shape-retaining memory, having a distal surface and a proximate surface defining a top end portion, a bottom end portion, and a curved portion, whereby said insertion guide conforms to the length and the contour of the respiratory tube, tube-connecting portion and the mask body in order to removably engage the LMA, wherein said elongated member includes
        a fulcrum member depending from said proximate surface and projecting laterally from said elongated member, including a curved surface for fitting the tube-connecting portion;
        a holder member extending from and connecting to said distal surface of said elongate member at a point above said fulcrum member, said holder member depending from said distal surface and projecting laterally in the same direction as said fulcrum member, and having a curved surface for fitting the respiratory tube; and,
        a scoop member having rounded, curved and flat surfaces for engaging a distal surface of the mask body, said scoop forming an integral and terminal portion of said bottom end portion.

8. The insertion guide device according to claim 7, wherein said top end portion is a rod having a rounded end.

9. A method for inserting a laryngeal mask airway (LMA) into the throat of a patient, comprising the steps of:
    engaging said LMA with said insertion guide device according to claim 7;
    inserting said LMA and said insertion guide into the throat of a patient;
    using the holder and the scoop of said insertion guide device to bend the LMA, while simultaneously using the fulcrum to push the LMA down into the patient's throat;
    positioning the LMA so that it covers the larynx of the patient;
    disengaging the holder and the fulcrum from their respective points on the LMA; and,
    removing said insertion guide device from the throat of the patient, leaving the LMA in place.

* * * * *